United States Patent [19]

Sinofsky

[11] Patent Number: 5,632,767
[45] Date of Patent: May 27, 1997

[54] LOOP DIFFUSERS FOR DIFFUSION OF OPTICAL RADIATION

[75] Inventor: Edward L. Sinofsky, Dennis, Mass.

[73] Assignee: Rare Earth Medical, Inc., West Yarmouth, Mass.

[21] Appl. No.: 467,414

[22] Filed: Jun. 6, 1995

Related U.S. Application Data

[63] Continuation-in-part of Ser. No. 303,605, Sep. 9, 1994.

[51] Int. Cl.$^6$ ................................................. A61B 17/36
[52] U.S. Cl. .............................. 607/89; 606/7; 606/15; 606/16; 606/17
[58] Field of Search ............................... 606/13–17, 7, 606/9–11; 607/88, 89

[56] References Cited

U.S. PATENT DOCUMENTS

| Re. 34,544 | 2/1994 | Spears | 604/20 |
|---|---|---|---|
| 3,417,745 | 12/1968 | Sheldon | 128/6 |
| 4,233,493 | 11/1980 | Nath | 219/354 |
| 4,336,809 | 6/1982 | Clark | 128/665 |
| 4,585,298 | 4/1986 | Mori | 350/96.1 |
| 4,660,925 | 4/1987 | McCaughan, Jr. | 350/96.15 |
| 4,860,743 | 8/1989 | Abela | 128/303.1 |
| 4,878,492 | 11/1989 | Sinofsky et al. | 128/303.1 |
| 5,053,033 | 10/1991 | Clarke | 606/3 |
| 5,133,709 | 7/1992 | Prince | 606/15 |
| 5,151,096 | 9/1992 | Khoury | 606/15 |
| 5,151,097 | 9/1992 | Daikuzono | 606/17 |
| 5,169,395 | 12/1992 | Narciso, Jr. | 606/7 |
| 5,196,005 | 3/1993 | Doiron et al. | 606/7 |
| 5,207,669 | 5/1993 | Baker et al. | 606/7 |
| 5,209,748 | 5/1993 | Daikuzono | 606/16 |
| 5,219,346 | 6/1993 | Wagnières et al. | 606/16 |
| 5,242,438 | 9/1993 | Saadatmanegh et al. | 606/15 |
| 5,269,777 | 12/1993 | Doiron et al. | 606/7 |
| 5,337,381 | 8/1994 | Bioswas et al. | 385/36 |
| 5,363,458 | 11/1994 | Pan et al. | 385/31 |
| 5,401,270 | 3/1995 | Muller et al. | 606/15 |
| 5,431,647 | 7/1995 | Purcell, Jr. et al. | 606/16 |
| 5,441,497 | 8/1995 | Narcisco, Jr. | 606/15 |

FOREIGN PATENT DOCUMENTS

| 0 214 712 | 3/1987 | European Pat. Off. . |
|---|---|---|
| 0 292 621 A1 | 11/1988 | European Pat. Off. . |
| 0 292 695 | 11/1988 | European Pat. Off. . |
| 0 439629 | 8/1991 | European Pat. Off. . |
| 0 598 984 | 6/1994 | European Pat. Off. . |
| WO92/17243 | 10/1992 | WIPO . |
| WO93/06888 | 4/1993 | WIPO . |
| WO93/19680 | 10/1993 | WIPO . |
| WO93/25155 | 12/1993 | WIPO . |
| WO94/17434 | 8/1994 | WIPO . |

OTHER PUBLICATIONS

U.S. application No. 08/303,605, Sinofsky, filed Sep. 9, 1994.

*Primary Examiner*—Robert L. Nasser
*Attorney, Agent, or Firm*—Thomas J. Engellenner; Lahive & Cockfield, LLP

[57] ABSTRACT

Methods and apparatus are disclosed for diffusing radiation from a optical fiber to provide a larger exposure area for phototherapy and to provide a substantially uniform energy distribution to a major portion of the exposure area. The invention is especially useful in constructing and implementing circumferential and/or sideways-emitting diffusive tip assemblies, or quasi-spherical diffusive tip assemblies for optical fibers to direct laser radiation in a radially outward pattern relative to the fiber's axis. In one aspect of the invention, a plurality of optically-transmissive fiber tip assemblies are employed to act as diffusers. The two or more fiber tip assemblies are deployed as loops which create a uniform illumination pattern. By "looping" or "folding" the fibers, a plurality of fibers can be deployed in conjunction with one another to create geometric exposure patterns with increased energy density while still avoiding "hot spots."

14 Claims, 3 Drawing Sheets

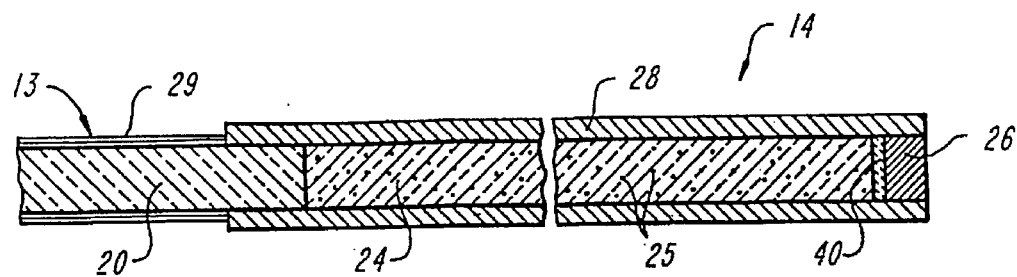
FIG. 4
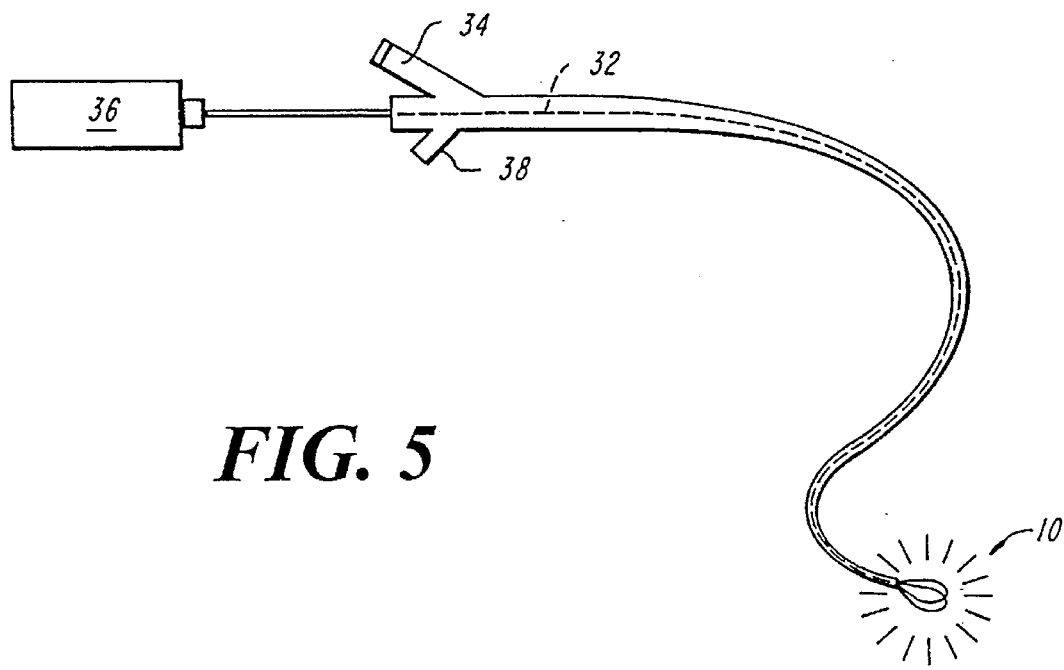
FIG. 5
FIG. 6
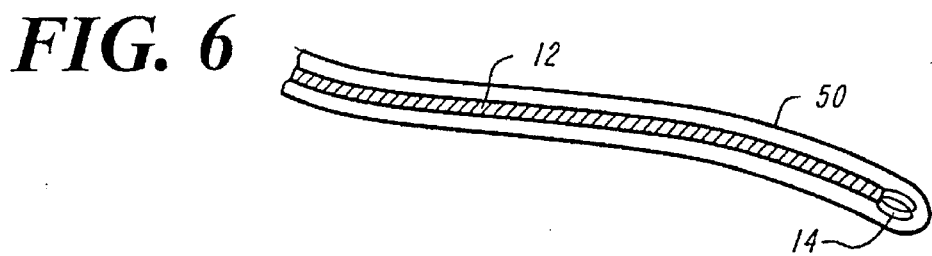

LOOP DIFFUSERS FOR DIFFUSION OF OPTICAL RADIATION

REFERENCE TO RELATED APPLICATIONS

This application is a continuation-in-part of U.S. patent application Ser. No. 8/303,605, filed Sep. 9, 1994, entitled "Phototherapy Methods and Apparatus."

BACKGROUND OF THE INVENTION

The technical field of this invention is phototherapy and, in particular, methods and devices which employ optical fibers and other flexible light waveguides to deliver radiation to a target site.

Fiber optic phototherapy is a increasing popular modality for the diagnosis and/or treatment of a wide variety of diseases. For example, in surgery, infrared laser radiation will often be delivered to a surgical site via a hand-held instrument incorporating an optically transmissive fiber in order to coagulate blood or cauterize tissue. Similar fiber optic delivery systems have been proposed for endoscopic or catheter-based instruments to deliver therapeutic radiation to a body lumen or cavity. U.S. Pat. No. 4,336,809 (Clark) and U.S. Reissue Pat. No. RE 34,544 (Spears) disclose that hematoporphyrin dyes and the like selectively accumulate in tumorous tissue and such accumulations can be detected by a characteristic fluorescence under irradiation with blue light. These patents further teach that cancerous tissue that has taken up the dye can be preferentially destroyed by radiation (typically high intensity red light) that is absorbed by the dye molecules during phototherapy.

Others have proposed the use of fiber-delivered radiation to treat artherosclerotic disease. For example, U.S. Pat. No. 4,878,492 (Sinofsky et al.) discloses the used of infrared radiation to heat blood vessel walls during balloon angioplasty in order to fuse the endothelial lining of the blood vessel and seal the surface. Another application of fiber-delivered radiation is disclosed in U.S. Pat. No. 5,053,033 (Clarke) which teaches that restenosis following angioplasty can be inhibited by application of UV radiation to the angioplasty site to kill smooth muscle cells which would otherwise proliferate in response to angioplasty-induced injuries to blood vessel walls.

Nonetheless, a number of problems limit the expanded use of fiber-optic phototherapy. Typically, an optical fiber emits light from only its end face. Thus, the emitted light tends to be at best divergent in a conical pattern and, therefore, exposes only a small region directly in from of the fiber's distal end. The small exposure area increases the power density at the fiber tip, thus limiting the power available for phototherapy since overheating of the target tissue must often be avoided.

Although "sideways-emitting" fibers have been proposed to permit greater flexibility in phototherapy, this approach still does not allow uniform irradiation of large volumes of tissue and can also be ill-suited for applications where circumferential uniformity is desired. Because sideways-emitting fibers expose limited regions, they do little to alleviate the problem of "hot spots" which limit the intensity of radiation which can be delivered via the fiber to the treatment site.

Others have proposed diffusive tips for optical fibers to enlarge the region which can be irradiated and/or reduce the potential for overexposure. However, diffusive tips have not been satisfactory for many therapeutic purposes because of their complexity of manufacture and/or because the radiation may not be scattered uniformly enough to alleviate the problem of "hot spots." Prior art diffusive tip structures have not be capable of delivering high power radiation, e.g., on the order of ten watts or more, to facilitate photocoagulation therapy or the like.

The use of diffusive tips in phototherapy is also limited by the amount of radiation that can be transmitted through a single diffuser assembly which is typically located at the distal end of an instrument. The diffuser structures are typically cylindrical or spherical in shape to facilitate a broadly-cast exposure pattern.

Accordingly, there exists a need for better apparatus for fiber optic phototherapy. In particular, diffusive tip assemblies which could provide broadly-cast exposure patterns in radial direction (e.g., sideways) relative to the instrument axis without hot spots would satisfy a long-felt need in the art. Moreover, light diffusing assemblies that could deliver greater amounts of energy in diffuse patterns would meet a particularly important need in the field of minimally-invasive phototherapeutic surgery.

SUMMARY OF THE INVENTION

Methods and apparatus are disclosed for diffusing radiation from a optical fiber to provide a larger exposure area for phototherapy. The methods and apparatus are particularly useful as part of a fiber optic-based medical laser system. The present invention can further provide substantially uniform energy distribution to a major portion of the exposure area. The invention is especially useful in constructing and implementing circumferential and/or sideways-emitting diffusive tip assemblies for or quasi-spherical diffusive tip assemblies optical fibers to direct laser radiation in a radially outward pattern relative to the fiber's axis. As used herein the term "optical fiber" is intended to encompass optically transmissive waveguides of various shapes and sizes.

In one aspect of the invention, a plurality of optically-transmissive fiber tip assemblies are disclosed to act as diffusers. The two or more fiber tip assemblies are deployed as loops which create a broadly east and relatively uniform illumination pattern. By "looping" or "folding" the fibers, a plurality of fibers can be deployed in conjunction with one another to create geometric exposure patterns with increased energy density while still avoiding "hot spots."

In another aspect of the invention, the loop diffusers can be incorporated into an endoscopic instrument or catheter. The diffusive elements can be initially deployed in a retracted position (largely within the body of the instrument) and then redeployed with the help of a control wire or the like in an expanded configuration. Thus, the two or more loops in the expanded configuration can create a "globe-like" diffuser assembly, or, if further extended, the loops can form a "heart shaped configuration. The invention thus permits a relatively small instrument to be enlarged to project a wide exposure area.

The individual loops each include a light transmissive, tubular housing aligned with, or adapted to receive, the distal end of a fiber and serve as a wave guide for light propagating through the fiber. In one embodiment, the tubular housing can be a hollow tube filled with a scattering medium and an optical fiber is joined to each end. Light propagating through the fibers will enter opposite ends of the housing and be scattered before reaching the other end In another embodiment, the assembly can be attached to a single fiber and further includes an end cap and a light scattering medium disposed within the housing such that light propagating through the fiber enters the scattering medium and a portion of the light escapes outward through the housing. In the one embodiment of the capped assembly, the end cap is a simple stopper and substantially all of the light eventually is scattered before it reaches the stopper. In another embodiment, the end cap can include a reflective surface such that as the light propagates through the fiber some of it is initially scattered by the scattering medium and exits radially, while another portion passes through the scattering medium and is reflected by the end cap for transmission through the scattering medium again.

In another aspect of the invention, the amount of incorporated scatterers and/or the length of the diffusive loop can be controlled such that the diffusion of the radiation beam during the initial and the reflected paths are complementary. By proper choice of parameters, the cumulative energy density or fluence along at least a portion of the length of the fiber tip can be rendered uniform.

In another aspect of the invention, novel materials and structures are disclosed for diffusive tip assemblies which further alleviate or reduce the potential for contact-adhesion between the tip and any body structure. This aspect of the invention is particularly useful to ensure that the diffusive tip does not accidentally bond to tissue. In one embodiment, fluoropolymer materials, such as Teflon® materials and the like, are disclosed as preferred materials for the tip enclosure because of their low contact-adhesion characteristics.

In yet another aspect of the invention, disposable sheaths are disclosed for use in conjunction with the diffuser assemblies. The outer sheath surrounds the entire optical transmission apparatus and ensures that the radiation-generating components do not come into direct contact with the patient's body structures. This permits reuse of the instrument. Only the sheath surrounding the apparatus needs to be disposed after each use.

The invention will next be described in connection with certain illustrated embodiments. However, to be clear that various changes and modifications can be made by those skilled in the art without departing from the spirit or scope of the invention.

BRIEF DESCRIPTION OF THE DRAWINGS

The invention may be more fully understood from the following description when read together with the accompanying drawings in which:

FIG. 4 is a cross-sectional view of another optical fiber diffusive tip assembly for use in the apparatus of FIG. 1;

FIG. 5 is a schematic view of the use of present invention as part of an endoscopic system; and FIG. 6 is a further cross-sectional view of an optical fiber and diffusive tip assembly in accordance with the present invention, further employing a disposable outer sheath.

DETAILED DESCRIPTION

Figure 1:
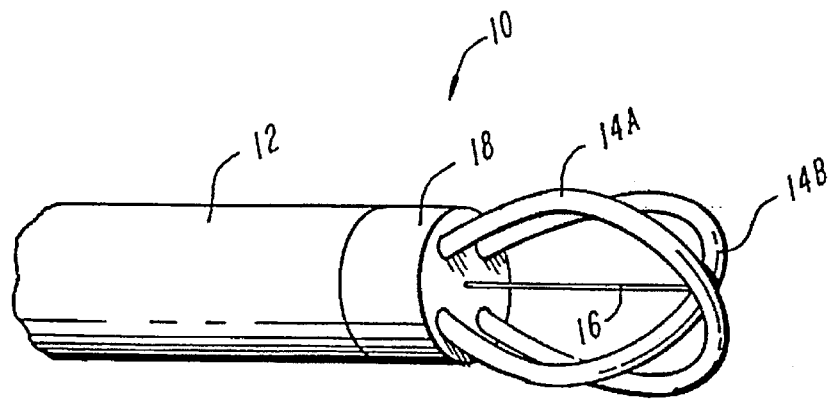
FIG. 1 is a schematic perspective view of a loop diffuser in accordance with the present invention.
Figure 2A:
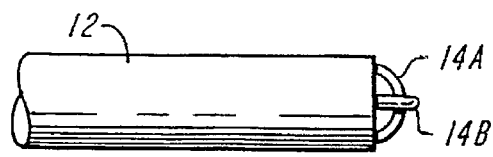
FIG. 2A is a side view of a loop diffuser in which the diffusive elements are fully retracted.
Figure 2B:
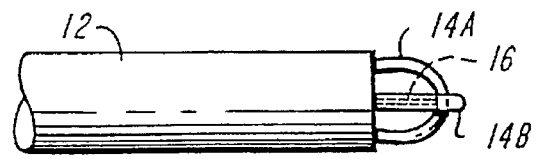
FIG. 2B is a side view similar to that of FIG. 2A in which the loop diffuser elements are partially deployed.
Figure 2C:
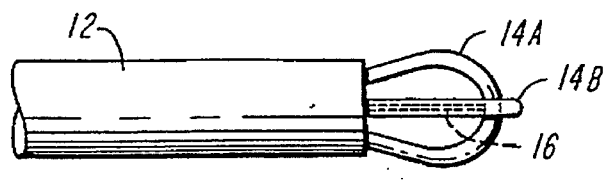
FIG. 2C is a further side view of the instrument in which the loop diffuser elements are fully deployed.

In FIG. 1, a phototherapeutic apparatus 10 is shown including a housing 12 having a plurality of light diffusing loops 14A, 14B which can be expanded out of, or retracted back into, the instrument housing 12 by control wire 16. As shown, the apparatus 10 can further include a radio opaque region 18 which facilitates location of the instrument by radiographic means. Although the apparatus is illustrated with only two loops, in some applications it can be desirable to have a great number of loops In FIGS. 2A–2C, the deployment of loop elements 14A and 14B is shown schematically. FIG. 2A illustrates a fully retracted mode in which most of the loop elements are withdrawn into the housing 12. In FIG. 2B, a control wire 16 has been moved partially forward and a larger portion of diffusive loop elements 14A and 14B projects outward from the housing 12. In FIG. 2C, the control wire has been slid forward even further and the loop elements 14a, 14b now are nearly fully deployed.

Figure 3A:
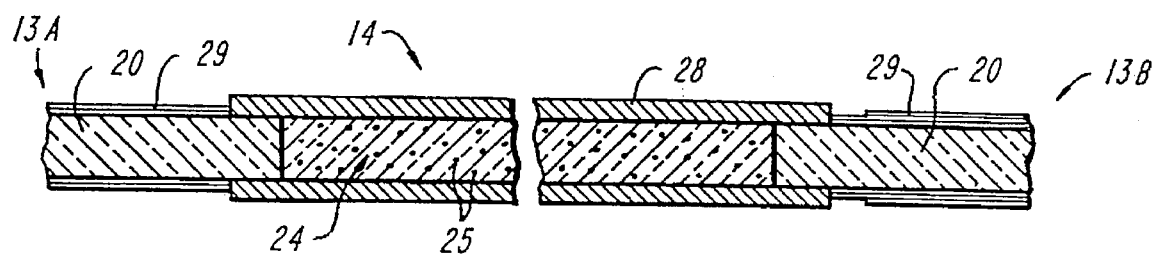
FIG. 3A is a cross-sectional view of an optical fiber diffusive tip assembly for use in the apparatus of FIG. 1.

In FIG. 3A, a truncated, cross-sectional view of a diffusive loop element 14 is shown connected to two optical fibers 13a and 13b, each having a light transmissive core 20A, 20B and a cladding/buffer coating 29. The end face of each fiber core 20A, 20B is inserted into a housing 28 which contains a scattering medium 24 with optional individual scatterer particles 25. Preferably, the medium 24 has a greater refractive index than the housing 28.

Figure 3B:
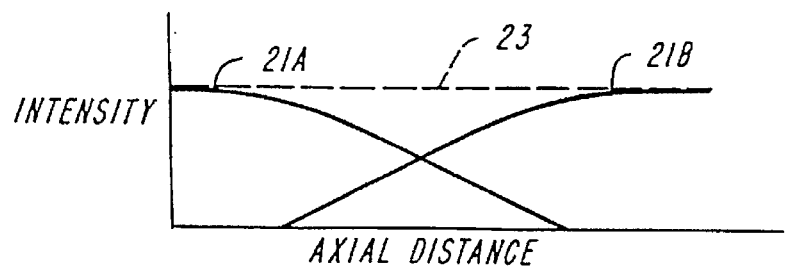
FIG. 3B is a graph of intensity vs. axial distance for the loop diffuser of FIG. 3A.

FIG. 3B is a graph of intensity vs. radial distance for two fibers as shown in FIG. 3A. The curve 21A illustrates the intensity of diffused radiation vs. axial length of one fiber while curve 21B represents a similar intensity distribution for a second fiber which has been deployed in an opposite configuration. The cumulative intensity distribution of these two fibers are shown by curve 23. By employing pairs of fibers that are joined in opposite directions, one can thus achieve nearly uniform distribution of the diffusive radiation.

A similar radiation distribution pattern can be achieved by employing a reflective end cap on each loop, as shown in FIG. 4. In this figure, a truncated, cross-sectional view of a diffusive loop element 14 is shown having an optical fiber 13 with a light transmissive core 20 and a cladding/buffer coating 29. The end face of fiber core 20 is inserted into a housing 28 which contains a scattering medium 24 with optional individual scatterer particles 25. Preferably, the medium 24 has a greater refractive index than the housing 28. At the distal end of the housing 28 an end plug 26 is disposed. Optionally, the end plug may also be fitted with a mirror reflector 40 to create a distribution pattern like that shown in FIG. 3B.

Light propagating through the optical fiber core 20 is transmitted into the scatterer medium and scattered in an cylindrical pattern along the length of the assembly 14. Each time the light encounters a scatterer particle, it is deflected and, at some point, the net deflection exceeds the critical angle for internal reflection at the interface between the housing 28 and the medium 24. When this happens the light will exit. The housing can either be made sufficiently long to ensure that virtually all of the light entering it is eventually scattered and diffused in a single path, or as noted above, a reflective mirror can be fitted to the distal end of each diffuser assembly. When a mirror is employed, light propagating through the medium 24 will be at least partially scattered before it reaches mirror 40. Light which does not exit during this initial pass through the tip will be reflected by mirror 40 and returned through the tip assembly. During the second pass, the remaining radiation (or at least a major portion of this returning radiation) again encounters the scatterers which provide further circumferential diffusion of the light.

An exemplary manufacturing process suitable for joining a diffuser assembly to a glass-clad or polymer-clad optical fiber having an outer diameter of about 50 to about 1000 micrometers can begin by stripping off the buffer from the end of the optical fiber, e.g., exposing about two or three millimeters of the inner fiber core and its cladding. (It is not necessary to strip the cladding away from the core.) Prior to stripping, the fiber end face preferably should be prepared and polished as known in the art to minimize boundary or interface losses. A transparent tubular structure which will form the housing for the scatterer medium is then slipped over the prepared fiber end and, preferably slid beyond the fiber end. For example, if a tip assembly of about 20 millimeters is desired, the tubing can be about 100 millimeters long and slid over about 75 millimeters of the fiber, leaving an empty lumen of about 25 millimeters in front of the fiber end face. In one preferred embodiment, the housing is Teflon® FEP tubing, available, for example, from Zeus Industries (Raritan, N.J.).

The assembly is then injected with a scatterer-loaded material, such as a silicone, epoxy or other polymeric material(if a solid diffuser is desired) or a suitable liquid, such as water or a deuterium oxide solution, containing colloidal scatterer particles, such as silica, alumina, or titania, (if a liquid diffuser is desired). One exemplary scatterer medium can be formulated by mixing 70 parts of clear silicone, Mastersil™ Formula 151-Clear (available from Masterbond, Inc. of Hackensack, N.J.) with one part of titania filled silicone, Mastersil™ Formula 151-White (also available from Masterbond), and a conventional silicone curing or hardening agent. The tube lumen should be completely filled with the silicone, epoxy or other carrier mixture to avoid entrapment of air bubbles. The reflector (e.g., an aluminum, gold or other reflector-coated plug) is inserted into the distal end of the tube. The reflector at the distal end of the scatterer tube can be a deposited metal or dielectric coating. In one preferred embodiment, a room temperature hardening agent is used and the diffuser assembly is simply allowed to solidify overnight.

It should be clear that the manufacturing processes described above are merely illustrative, and various alternative techniques can be practiced to construct the fiber tip assemblies of the present invention. For example, automated extrusion methods and/or injection molding approaches can be employed to mass produce fibers with integral diffusive tip assemblies.

The amount of scatterer incorporated into the diffusive tip assembly will vary with the carrier and the desired length, and can therefore be adjusted to meet particular applications. Different scatterers may be more or less useful in particular applications. Table 1 below illustrates certain relevant characteristics of three different scatterer compositions:

TABLE 1

| Scatterer Composition | Scatterer Characteristics | |
|---|---|---|
| | Density (grams/cc) | Transmission Spectrum (wavelength in micrometers) |
| $TiO_2$ | 4.0 | .45–11 |
| $SiO_2$ | 2.1 | .2–7 |
| $Al_2O_3$ | 3.6 | .2–9 |

In certain applications, it may be desirable to mix two or more scatterer compositions together to achieve blended characteristics.

Liquid scatterer compositions can be used to extend phototherapy into the ultraviolet (UV) and infrared (IR) regions of the spectrum. In particular, structures employing deuterium oxide and other heavy water solutions are useful to transmit IR light with low losses and minimal tip heating. Distilled water suspensions of scatterers or simply water or acetic acid can be useful in UV light delivery.

The above-described manufacturing techniques were used to produce diffusing tips joined to fibers ranging from about 100 to about 600 micrometers in diameter. When fiber bundles are joined to the diffuser tip, the individual fibers can be even smaller, e.g., as small as 25 micrometers in diameter. The cylindrical light-diffusing assemblies can be used to produce axial exposure patterns of about 2 cm to about 4 cm in length and nearly spherical exposure patterns.

The devices of the present invention can be used for various therapeutic purposes. One application is photodynamic therapy (PDT), a form of light-activated chemotherapy. In this approach, photosensitive dyes are delivered by injection or other vehicles such that the dye is preferentially accumulated in cancer cells. When the cells which have taken up the dye are irradiated at an appropriate wavelength (e.g., with red light), a photochemical reaction occurs that yields radicals (usually singlet oxygen) which poison the cell. Thus, the present invention further encompasses the use of diffused radiation to activate photosensitive dyes. One advantage of the present invention is that it permits PDT at remote treatment sites via a catheter, trocar, hollow needle or other hand held instrument in a minimally invasive manner because diffusive fiber tip assemblies can now be constructed with outer diameters on the order of only a few hundred micrometers. The invention is particularly useful in illuminating spherical or hollow organs such as the bladder, stomach or uterus.

The present invention also encompasses the use of diffuse radiation in photocoagulation and/or hypodermic therapy of tumors and hyperplasia. For example, the phototherapy apparatuses described above can be used to treat liver, pancreatic or prostate tumors, or benign prostate hyperplasia. The application of diffuse radiation to heat prostate tissue can be used in lieu of transurethral resection of the prostate, balloon dilatation of the prostate or ultrasonic hyperthermia. In particular, the directional probes described above can be especially useful in improving the outcome of prostate treatment by heating more tissue directly in less time, and in distributing irradiation over a larger volume of prostatic tissue, thus increasing the therapeutic heating effects while reducing the risk of overheating damage to surrounding tissue structures such as the sphincter. The invention further permits interstitial laser coagulation of hepatic and pancreatic tumors. The desired effects are achieved by thermal destruction of cancerous tissue by depositing laser radiation via a diffusive fiber tip carrier by a hypodermic needle or similar instrument inserted percutaneously into the tumor. In each of these procedures, therapy can be delivered while the patient is awake; general anesthesia as well as open surgery are avoided.

In heat-based phototherapy techniques, the diffusive fiber tip assemblies of the present invention allow for the formation of large distributed heat sources within the target tissue. The invention significantly alters the rate of heat deposition in tissue, especially in the regions immediately surrounding the fiber tip, where tissue overheating and/or carbonization would limit the effectiveness and inhibit efficient heat transfer. Since the radiation is distributed by the diffuser assembly over a larger volume of tissue, more tissue is heated directly and there is less need to rely on convective or conductive heat transfer through nearby tissue to reach the periphery of the tumor.

Moreover, the materials disclosed herein for the diffusive tips and jackets further enhance the therapeutic effects by permitting high radiation transmission and low absorption, thereby ensuring the tip assembly itself does not overheat during usage. In addition, the use of Teflon® tubes and/or coatings further improve the procedures by avoiding the problem of tip fusion or contact-adhesion between the tip assembly and biological tissue during usage. It has been found that Teflon® FEP materials (polyperfluoroethylene-propylene copolymers) are preferable for most applications because they do not discolor if they are etched prior to loading with the scatterer medium, although Teflon® PFA materials (polytetrafluoroethylene polymers with perfluoroalkoxy side chains) and Teflon® PTFE (polytetrafluoroethylene) and other fluoropolmers may also be useful.

In FIG. 5, the loop diffuser apparatus of the present invention 10 is shown schematically in operation. The diffuser apparatus 10 is coupled to a source of phototherapeutic radiation 36 (e.g., a laser) and positioned within a patient's body to provide phototherapy. As shown in FIG. 5, the diffuser assembly can be designed to fit within the instrument channel of an endoscope 32. The endoscope can further include viewing means 34 and/or at least one additional channel 38 for the introduction of irrigation saline or therapeutic solutions. Alternatively, the diffusing assemblies of the present invention can be incorporated into catheter-type instruments that are introduced into the patient's body without the assistance of an endoscopic channel.

In FIG. 6, an outer jacket (e.g., of Teflon® material) is shown disposed about the apparatus to encase the fiber 12 and loop diffuser assembly 14. The outer sheath surrounds the entire optical transmission apparatus and ensures that the radiation-generating components do not come into direct contact with the patient's body and, thereby, permits reuse of the instrument. Only the outer sheath 50 needs to be disposed after each use.

I claim:

1. A fiber optic transmission and diffusion apparatus comprising:

a plurality of optical fibers having proximal and distal ends, the proximal ends adapted for coupling to a source of phototherapeutic radiation;

wherein each optical fiber has connected to its distal end a tip assembly for directing radiation outward, each tip assembly being arranged in a loop configuration to form a loop diffuser; and a housing surrounding the optical fibers and each of said loop diffusers, wherein each of said loop diffusers are expandable out of and retractable back into said housing.

2. The apparatus of claim 1 wherein each tip assembly further comprises a light scattering medium which directs radiation entering the tip assembly outward.

3. The apparatus of claim 1 wherein the apparatus further comprises a control means for moving of each said loop diffusers from a retracted to an expanded state.

4. The apparatus of claim 1 wherein of each the tip assemblies further comprise a tip enclosure containing a scattering medium therein.

5. The apparatus of claim 4 wherein the scattering medium further comprises a polymeric material which has light scattering particles dispersed therein.

6. The apparatus of claim 5 wherein the scatterer particles are chosen from the group consisting of alumina, silica, and titania compounds and mixtures thereof.

7. The apparatus of claim 5 wherein the tip enclosure further comprises a radiation transmissive fluorocarbon polymer.

8. A fiber optic transmission apparatus comprising:

at least one optical fiber having proximal and distal ends, the proximal end adapted for coupling to a source of phototherapeutic radiation;

wherein each optical fiber has connected to its distal end a tip assembly for directing the radiation outward, the tip assembly being arranged in a loop configuration, and wherein each optical fiber is connected to a different tip assembly;

wherein each tip assembly further comprises a tip enclosure containing a scattering medium further comprises a polymeric material which has light scattering particles dispersed therein;

wherein the tip assembly also further comprises a reflective end cap; and a housing surrounding the at least one optical fiber and receiving the end cap, and at least a portion of each tip assembly.

9. The apparatus of claim 8 wherein each of the tip assemblies further comprise a tip enclosure containing a scattering medium therein.

10. The apparatus of claim 9 wherein the scattering medium further comprises a polymeric material which has light scattering particles dispersed therein.

11. The apparatus of claim 10 wherein the scatterer particles are chosen from the group consisting of alumina, silica, and titania compounds and mixtures thereof.

12. The apparatus of claim 9 wherein the tip enclosure further comprises a radiation transmissive fluorocarbon polymer.

13. A method of phototherapy comprising the steps of:

placing a light diffusive assembly in proximity to a treatment site, the assembly comprising a plurality of light transmissive loop diffuser elements, each loop element further comprising a light scattering medium, such that radiation propagating through the medium is scattered outward, providing at least one source of therapeutic radiation to the diffusive assembly via an optical fiber connected to each loop element, disposing said loop elements initially in a retracted state and then redeploying them in an expanded state; and activating said radiation source to effect treatment with diffused radiation.

14. The method of claim 13 wherein the method further comprises providing at least two sources of radiation to said diffuser element.

* * * * *

UNITED STATES PATENT AND TRADEMARK OFFICE
CERTIFICATE OF CORRECTION

PATENT NO. : 5,632,767
DATED : May 27, 1997
INVENTOR(S) : Edward L. Sinofsky

It is certified that error appears in the above-indentified patent and that said Letters Patent is hereby corrected as shown below:

At column 1, line 49, please replace "in from of" with --in front of--;

At column 7, line 59, please replace "of each the" with --each of the--.

Signed and Sealed this

Twenty-first Day of October 1997

*Attest:*

BRUCE LEHMAN

*Attesting Officer*      *Commissioner of Patents and Trademarks*